US006221614B1

(12) United States Patent
Prusiner et al.

(10) Patent No.: US 6,221,614 B1
(45) Date of Patent: *Apr. 24, 2001

(54) REMOVAL OF PRIONS FROM BLOOD, PLASMA AND OTHER LIQUIDS

(75) Inventors: Stanley B. Prusiner, San Francisco; Jiri G. Safar, Concord, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/235,372

(22) Filed: Jan. 20, 1999

Related U.S. Application Data

(63) Continuation-in-part of application No. 09/151,057, filed on Sep. 10, 1998, which is a continuation-in-part of application No. 09/026,957, filed on Feb. 20, 1998, which is a continuation-in-part of application No. 08/804,536, filed on Feb. 21, 1997, now Pat. No. 5,891,641.

(51) Int. Cl.$^7$ ................................................ G01N 33/53

(52) U.S. Cl. ............................ 435/7.1; 424/520; 436/525

(58) Field of Search ............................. 435/7.1; 530/350, 530/412, 413, 123; 424/520; 436/525, 526

(56) References Cited

U.S. PATENT DOCUMENTS

| | | | |
|---|---|---|---|
| 4,300,905 | 11/1981 | Bleisteiner et al. | 23/230 B |
| 4,320,086 | 3/1982 | Reiss | 422/56 |
| 4,806,627 | 2/1989 | Wisniewski et al. | 530/387 |
| 5,521,060 | 5/1996 | Hoenes et al. | 435/4 |
| 5,565,186 | 10/1996 | Prusiner et al. | 424/9.2 |
| 5,846,533 | * 12/1998 | Prusiner et al. | 424/130.1 |
| 5,858,326 | 1/1999 | Kislievsky et al. | 424/9.2 |
| 5,891,641 | 4/1999 | Prusiner et al. | 435/7.1 |
| 5,977,324 | * 11/1999 | Prusiner et al. | 530/418 |

FOREIGN PATENT DOCUMENTS

| | | |
|---|---|---|
| WO 93/10227 | 5/1993 | (WO) . |
| WO 93/23432 | 11/1993 | (WO) . |
| WO 97/43649 | 11/1997 | (WO) . |
| WO 99/42487 | 8/1999 | (WO) . |

OTHER PUBLICATIONS

Gabizon et al. Immunoaffinity purification and neutralization of scrapie prion infectivity. Sep. 1988. Proc. Natl. Acad. Sci. USA, vol. 85, pp. 6617–6621.*

Korth et al. Prion (PrPsc)–specific epitope defined by a monoclonal antibody. Nov. 6, 1997. Nature, vol. 390, pp. 74–77.*

Setchel, C.H. Magnetic separations in biotechnology—a review. 1985. J. Chem. Tech. Biotechnol., vol. 35B, pp. 175–182.*

Karlsson et al. Analysis and isolation of human transferrin receptor using the OKT–9 monoclonal antibody covalently crosslinked to magnetic beads. 1991. Analytical Biochemistry, vol. 199, pp. 219–222.*

Anderson et al., (1996) "Transmission dynamics and epidemiology of BSE in British cattle," *Nature* 382: 779–88.

Barry, R.A., et al., (1986) "Monoclonal Antibodies to the Cellular and Scrapie Prion Proteins," *Journal of Infectious Diseases* 154:518–521.

Basler et al., (1986) "Scrapie and Cellular PrP Isoforms Are Encoded by the Same Chromosomal Gene," *Cell* 46: 417–28.

Bendheim, et al., (1984) "Antibodies to a Scrapie Prion Protein," *Nature* 310:418–421.

Bode et al., (1985) "Characterization of Antisera Against Scrapie–Associated Fibrils (SAF) from Affected Hamster and Cross–Reactivity with SAF from Scarpie–Affected Mice and from Patients with Creutzfeldt–Jacob Disease," *J. Gen. Virol.* 66:2471–2478.

Bolton et al., (1982) "Identification of a Protein That Purifies with the Scrapie Prion," *Science* 218: 1309–11.

Brown et al., (1992) "'Friendly Fire' in Medicine: Hormones, Homografts, and Creutzfeldt–Jakob Disease," *Lancet* 340: 24–27.

Buchanan et al., (1991) "Mortality, Neoplasia, and Creutzfeldt–Jakob Disease in Patients Treated with Human Pituitary Growth Hormone in the United Kingdom", *BMJ* 302:824–828.

Bueler et al., (1992) "Normal Development and Behavior of Mice Lacking the Neuronal Cell–surface PrP Protein," *Nature* 356:577–582.

Carter, et al., (1992) "High Level *Escherichia coli* Expression and Production of a Bivalent Humanized Antibody Fragment," *Biotechnology* 10:163–7.

Cochius et al., (1992) "Creutzfeldt–Jakob Disease in a Recipient of Human Pituitary–Derived Gonadotrophin: A Second Case," *J. Neurol. Neurosurg. Psychiatry* 55:1094–1095.

Cochius et al., (1990) "Creutzfeldt–Jakob Disease in a Recipient of Human Pituitary–Derived Gonadotrophin," *Aust. N.Z. J. Med.* 20:592–593.

Collinge, et al., (1996) "Prion protein gene analysis in new variant cases of Creutzfeldt–Jakob disease," *Lancet* 348: 56.

Gajdusek, D.C., (1977) "Unconventional Viruses and the Origin and Disappearance of Kuru," *Science* 197:943–960.

(List continued on next page.)

*Primary Examiner*—Ardin H. Marschel
*Assistant Examiner*—Nancy Ogihara
(74) *Attorney, Agent, or Firm*—Karl Bozicevic; Bozicevic, Field & Francis LLP

(57) ABSTRACT

Devices such as flow through columns, substrates such as spherical polymer beads, and methods of using such to remove prions from any liquid sample are disclosed. A surface of a substrate is coated with a prion complexing agent, such as a salt of phosphotungstic acid. Blood or plasma passing through a column containing beads coated with prion complexing agent are rendered prion free.

9 Claims, No Drawings

OTHER PUBLICATIONS

Gibbs, Jr. et al., (1993) "Creutzfeldt–Jakob Disease Infectivity of Growth Hormone Derived from Human Pituitary Glands," *N. Engl. J. Med.* 328:358–359.

Goldfarb et al., (1992) "Fatal Familial Insomnia and Familial Creutzfeldt–Jakob Disease: Disease Phenotype Determined by a DNA Polymorphism," *Science* 258:806–808.

Healy et al., "Creutzfeldt–Jakob Disease After Pituitary Gonadotrophins: The Prion is the Problem," *BMJ* (1993) 307:517–518.

Hsiao et al., (1994) "Serial transmission in rodents of neurodegeneration from transgenic mice expressing mutant rion protein," *Proc. National Acad. Sci. USA* 91:9126–30.

Kascsak, R.J., et al., (1987) "Mouse Polyclonal and Monoclonal Antibody to Scrapie–Associated Fibril Proteins" *Journal of Virology* 61:3688–3693.

Lasmezas et al., (1993) "Recombinant Human Growth Hormone and Insulin–Like Growth Factor I Induce PRP Gene Expression in PC12 Cell," *Biochem. Biophys. Res. Commun.* 196:1163–1169.

McKinley et al., (1983) "A Protease–Resistant Protein is a Structural Component of the Scrapie Prion," *Cell* 35:57–62.

Mehlhorn et al., (1996) "High–Level Expression and Characterization of a Purified 142–Residue Polypeptide of the Prion Protein," *Biochemistry* 35: 5528–37.

Meyer et al., (1986) "Separation and Properties of Cellular and Scrapie Prion Proteins," *Proc. Natl. Acad. Sci. USA* 83: 2310–2314.

Oesch, et al., (1985) "A Cellular Gene Encodes Scrapie PrP 27–30 Protein," *Cell* 40: 735–46.

Pan, et al., (1993) "Conversion of α–helices into β–sheets features in the formation of the scrapie prion proteins," *Proc. Natl. Acad. Sci. USA* 90:10962–66.

Pan, et al., (1992) "Purification and Properties of the Cellular Prion Protein from Syrian Hamster Brain," *Protein Sci.* 1:1343–1352.

Prusiner, S.B., et al., (1983) "Scrapie prions aggregate to form amyloid–like birefringent rods," *Cell* 35: 349–58.

Prusiner, S.B. et al., "Biology of Prions," *The Molecular and Genetic Basis of Neurological Disease*, 2nd Edition, Chap. 7, pp. 103–143 (1997).

Rogers et al., (1991) "Epitope Mapping of the Syrian Hamster Prion Protein Utilizing Chimeric and Mutant Genes in a Vaccinia Virus Expression System," *J. Immunol.* 147: 3568–74.

Rogers, et al., (1993) "Conversion of truncated and elongated prion proteins into the scrapie isoform in cultured cells," *Proc. Natl. Acad. Sci. USA* 90:3182–6.

Safar et al. J., (1993) "Conformational Transitions, Dissociation, and Unfolding of Scrapie Amyloid (Prion) Protein," *J. Biol. Chem.* 268: 20276–84.

Safar, et al., (1990) "Scrapie–associated precursor proteins: Antigenic relationship between species and immunocytochemical localization in normal, scrapie, and Creutzfeldt–Jakob disease brains," *Neurology* 40:513–7.

Schmerr, Mary Jo et al., (1996) "Improvements in a Competition Assay to Detect Scrapie Prion Protein by Capillary Eletrophoresis", *Journal of Chromatography B* 681:29–35.

Serban et al, (1990) "Rapid Detection of Creuzfeldt–Jakob Disease and Scrapie Prion Proteins," *Neurology* 40:110–7.

Stahl et al., (1993) "Structural Studies of the Scrapie Prion Protein Using Mass Spectrometry and Amino Acid Sequencing," *Biochemistry* 32: 1991–2002.

Taraboulos et al., (1992) "Regional Mapping of Prion Proteins in Brain," *Proc. Natl. Acad. Sci. USA* 89:7620–7624.

Turk, et al., (1988) "Purification and Properties of the Cellular and Scrapie Hamster Prion Proteins," *Eur. J. Biochem.* 176:21–30.

Wilesmith and Wells, (1991) "Bovine Spongiform Encephalopathy," *Curr. Topics Microbiol. Immunol.* 172 21–38.

Wilesmith, "Bovine Spongiform Encephalopathy," *Methods in Molecular Medicines: Prion Diseases*, pp. 155–73. (1996).

Williamson, et al., (1996) "Circumventing tolerance to generate autologous monoclonal antibodies to the prion protein," *Proc. Natl. Acad. Sci. USA* 93: 7279–82.

Yokoyama, Takashi, et al., (1996) "Immunoreactivity of Specific Epitopes of $PrP^{Sc}$ is Enhanced by Pretreatment in a Hydrated Autoclave", *Clinical and Diagnostic Laboratory Immunology* 3(4):470–471.

Alpatove, M. N. et al., Chemical Abstracts, vol. 121, No. 16 ( Oct. 17, 1994).

Kamada et al., Bull. Chem. Soc. Jpn., 66:3565–3570 (1993).

Kimberlin et al., Antiomicrobial Agents and Chemotherapy, 30:(3):409–413 (Sept. 1986).

Safar et al., Nature Medicine, 4(10): 1157–1165 (Oct. 1998).

Saidkhanov et al., Journal of Molecular Catalysis, 21:365–373 (1983).

* cited by examiner

REMOVAL OF PRIONS FROM BLOOD, PLASMA AND OTHER LIQUIDS

CROSS-REFERENCE

This application is a continuation-in-part application of Ser. No. 09/151,057, filed Sep. 10, 1998, which is a continuation-part of Ser. No. 09/026,957, filed Feb. 20, 1998, which is a continuation-in-part of Ser. No. 08/804,536, filed Feb. 21, 1997 (issued as U.S. Pat. No. 5,891,641 on Apr. 6, 1999) all of which applications are incorporated herein by reference in its entirety and to which applications we claim priority under 35 U.S.C. §120.

GOVERNMENT RIGHTS

The United States Government may have certain rights in this application pursuant to Grant No. AG02132 awarded by the National Institutes of Health.

FIELD OF THE INVENTION

The invention relates generally to methods of purifying samples and particularly to methods of removing prions from blood and blood products.

BACKGROUND OF THE INVENTION

Prions are infectious pathogens that cause central nervous system spongiform encephalopathies in humans and animals. Prions are distinct from bacteria, viruses and viroids. The predominant hypothesis at present is that no nucleic acid component is necessary for infectivity of prion protein. Further, a prion which infects one species of animal (e.g., a human) will not infect another (e.g., a mouse).

A major step in the study of prions and the diseases that they cause was the discovery and purification of a protein designated prion protein ("PrP") [Bolton et al., *Science* 218:1309–11 (1982); Prusiner et al., *Biochemistry* 21:6942–50 (1982); McKinley et al., *Cell* 35:57–62 (1983)]. Complete prion protein-encoding genes have since been cloned, sequenced and expressed in transgenic animals. $PrP^C$ is encoded by a single-copy host gene [Basler et al., *Cell* 46:417–28 (1986)] and is normally found at the outer surface of neurons. A leading hypothesis is that prion diseases result from conversion of $PrP^C$ into a modified form called $PrP^{Sc}$.

It appears that the scrapie isoform of the prion protein ($PrP^{Sc}$) is necessary for both the transmission and pathogenesis of the transmissible neurodegenerative diseases of animals and humans. See Prusiner, S. B., "Molecular biology of prion disease," *Science* 252:1515–1522 (1991). The most common prion diseases of animals are scrapie of sheep and goats and bovine spongiform encephalopathy (BSE) of cattle [Wilesmith, J. and Wells, *Microbiol. Immunol.* 172:21–38 (1991)]. Four prion diseases of humans have been identified: (1) kuru, (2) Creutzfeldt-Jakob Disease (CJD), (3) Gerstmann-Strassler-Scheinker Disease (GSS), and (4) fatal familial insomnia (FFI) [Gajdusek, D.C., *Science* 197:943–960 (1977); Medori et al., *N. Engl. J. Med.* 326:444–449 (1992)]. The presentation of human prion diseases as sporadic, genetic and infectious illnesses initially posed a conundrum which has been explained by the cellular genetic origin of PrP.

Most CJD cases are sporadic, but about 10–15% are inherited as autosomal dominant disorders that are caused by mutations in the human PrP gene [Hsiao et al., *Neurology* 40:1820–1827 (1990); Goldfarb et al., *Science* 258:806–808 (1992); Kitamoto et al., *Proc. R. Soc. Lond.* 343:391–398.

Iatrogenic CJD has been caused by human growth hormone derived from cadaveric pituitaries as well as dura mater grafts [Brown et al., *Lancet* 340:24–27 (1992)]. Despite numerous attempts to link CJD to an infectious source such as the consumption of scrapie infected sheep meat, none has been identified to date [Harries-Jones et al., *J. Neurol. Neurosurg. Psychiatry* 51:1113–1119 (1988)] except in cases of iatrogenically induced disease. On the other hand, kuru, which for many decades devastated the Fore and neighboring tribes of the New Guinea highlands, is believed to have been spread by infection during ritualistic cannibalism [Alpers, M. P., *Slow Transmissible Diseases of the Nervous System*, Vol. 1, S. B. Prusiner and W. J. Hadlow, eds. (New York: Academic Press), pp. 66–90 (1979)].

The initial transmission of CJD to experimental primates has a rich history beginning with William Hadlow's recognition of the similarity between kuru and scrapie. In 1959, Hadlow suggested that extracts prepared from patients dying of kuru be inoculated into nonhuman primates and that the animals be observed for disease that was predicted to occur after a prolonged incubation period [Hadlow, W. J., *Lancet* 2:289–290 (1959)]. Seven years later, Gajdusek, Gibbs and Alpers demonstrated the transmissibility of kuru to chimpanzees after incubation periods ranging form 18 to 21 months [Gajdusek et al., *Nature* 209:794–796 (1966)]. The similarity of the neuropathology of kuru with that of CJD [Klatzo et al., *Lab Invest.* 8:799–847 (1959)] prompted similar experiments with chimpanzees and transmissions of disease were reported in 1968 [Gibbs, Jr. et al., *Science* 161:388–389 (1968)]. Over the last 25 years, about 300 cases of CJD, kuru and GSS have been transmitted to a variety of apes and monkeys.

The expense, scarcity and often perceived inhumanity of such experiments have restricted this work and thus limited the accumulation of knowledge. While the most reliable transmission data has been said to emanate from studies using nonhuman primates, some cases of human prion disease have been transmitted to rodents but apparently with less regularity [Gibbs, Jr. et al., *Slow Transmissible Diseases of the Nervous System*, Vol. 2, S. B. Prusiner and W. J. Hadlow, eds. (New York: Academic Press), pp. 87–110 (1979); Tateishi et al., *Prion Diseases of Humans and Animals*, Prusiner et al., eds. (London: Ellis Horwood), pp. 129–134 (1992)].

The infrequent transmission of human prion disease to rodents has been cited as an example of the "species barrier" first described by Pattison in his studies of passaging the scrapie agent between sheep and rodents [Pattison, I. H., *NINDB Monograph* 2, D. C. Gajdusek, C. J. Gibbs Jr. and M. P. Alpers, eds. (Washington, D.C.: U.S. Government Printing), pp. 249–257 (1965)]. In those investigations, the initial passage of prions from one species to another was associated with a prolonged incubation time with only a few animals developing illness. Subsequent passage in the same species was characterized by all the animals becoming ill after greatly shortened incubation times.

The molecular basis for the species barrier between Syrian hamster (SHa) and mouse was shown to reside in the sequence of the PrP gene using transgenic (Tg) mice [Scott et al., *Cell* 59:847–857 (1989)]. SHaPrP differs from MoPrP at 16 positions out of 254 amino acid residues [Basler et al., *Cell* 46:417–428 (1986); Locht et al., *Proc. Natl. Acad. Sci. USA* 83:6372–6376 (1986)]. Tg(SHaPrP) mice expressing SHaPrP had abbreviated incubation times when inoculated with SHa prions. When similar studies were performed with mice expressing the human, or ovine PrP transgenes, the species barrier was not abrogated, i.e., the percentage of animals which became infected were unacceptably low and the incubation times were unacceptably long. Thus, it has not been possible, for example in the case of human prions, to use transgenic animals (such as mice containing a PrP gene of another species) to reliably test a sample to determine if that sample is infected with prions. The seriousness of the health risk resulting from the lack of such a test is exemplified below.

More than 45 young adults previously treated with HGH derived from human pituitaries have developed CJD [Koch et al., *N. Engl. J. Med.* 313:731–733 (1985); Brown et al., *Lancet* 340:24–27 (1992); Fradkin et al., *JAMA* 265:880–884 (1991); Buchanan et al., *Br. Med. J.* 302:824–828 (1991)]. Fortunately, recombinant HGH is now used, although the seemingly remote possibility has been raised that increased expression of wtPrP$^C$ stimulated by high HGH might induce prion disease [Lasmezas et al., *Biochem. Biophys. Res. Commun.* 196:1163–1169 (1993)]. That the HGH prepared from pituitaries was contaminated with prions is supported by the transmission of prion disease to a monkey 66 months after inoculation with a suspect lot of HGH [Gibbs, Jr. et al., *N. Engl. J. Med.* 328:358–359 (1993)]. The long incubation times associated with prion diseases will not reveal the full extent of iatrogenic CJD for decades in thousands of people treated with HGH worldwide. Iatrogenic CJD also appears to have developed in four infertile women treated with contaminated human pituitary-derived gonadotrophin hormone [Healy et al., *Br. J. Med.* 307:517–518 (1993); Cochius et al., *Aust. N.Z. J. Med.* 20:592–593 (1990); Cochius et al., *J. Neurol. Neurosurg. Psychiatry* 55:1094–1095 (1992)] as well as at least 11 patients receiving dura mater grafts [Nisbet et al., *J. Am. Med. Assoc.* 261:1118 (1989); Thadani et al., *J. Neurosurg.* 69:766–769 (1988); Willison et al., *J. Neurosurg. Psychiatric* 54:940 (1991); Brown et al., *Lancet* 340:24–27 (1992)]. These cases of iatrogenic CJD underscore the need for screening pharmaceuticals that might possibly be contaminated with prions.

Recently, two doctors in France were charged with involuntary manslaughter of a child who had been treated with growth hormones extracted from corpses. The child developed Creutzfeldt-Jakob Disease. (See *New Scientist*, Jul. 31, 1993, page 4). According to the Pasteur Institute, since 1989 there have been 24 reported cases of CJD in young people who were treated with human growth hormone between 1983 and mid-1985. Fifteen of these children have died. It now appears as though hundreds of children in France have been treated with growth hormone extracted from dead bodies at the risk of developing CJD (see *New Scientist*, Nov. 20, 1993, page 10.) In view of such, there clearly is a need for a convenient, cost-effective means for removing prions which cause CJD from blood and blood products. The present invention provides such a method.

SUMMARY OF THE INVENTION

Prions are removed from biological materials such as blood and plasma by contacting these materials with a complexing agent, such as a biological agent (e.g. an antibody) or a chemical agent (e.g. a substrate comprised of sodium phosphotungstate) which binds prions.

The substrate may be used in any configuration which allows removal of the prion from the biological materials, such as spherical polymer beads which are coated with a complexing agent and housed in a column through which the blood, plasma or other material suspected of containing prions is allowed to flow.

An object of the invention is to provide a simple and economical means for removing prions from a material.

An advantage of the invention is that blood products which might contain prions can be certified as prion free when processed via the invention.

A feature of the invention is that prions selectively bind to chemical agents such as heteropoly acids or metal salts of heteropoly acids. A preferred chemical agent for use in the methods of the invention is sodium phosphotungstate.

Another feature of the invention is that prions bind selectively to biological agents such as peptides, small molecules and selective PrP$^{Sc}$ binding antibodies.

An aspect of the invention is a substrate which may be in the form of spherical polymer beads having a complexing agent coated on their surface. In a particular embodiment, spherical beads have a ferromagnetic metal core which allows separation of the beads using magnetic forces and have an inert polymer coating the metal core with the polymer coated with a metal salt of phosphotungstate acid.

Another aspect of the invention is blood and blood products such as plasma which have been treated with the method of the invention.

Yet another aspect of the invention is a filter membrane used to remove prions from biological materials using methods such as hemofiltration.

Yet another aspect of the invention is a device comprised of a housing (preferably cylindrical) having surfaces therein coated with a composition which binds PrP$^{Sc}$ e.g. spherical lead surfaces coated with sodium phosphotungstate.

These and other objects, aspects, advantages, and features of the invention will become apparent to those persons skilled in the art upon reading the details of the binding agents, devices and methods as more fully described below.

DETAILED DESCRIPTION OF PREFERRED EMBODIMENTS

Before the present methods and devices are disclosed and described, it is to be understood that this invention is not limited to particular complexing agents, proteins, labels, assays or method as such may, of course vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided are subject to change if it is found that the actual date of publication is different from that provided here.

DEFINITIONS

The term "complexing agent" is used herein to refer to any material which binds or complexes selectively with either the constrictive conformation of a protein (e.g. with PrP$^{Sc}$) and/or with the relaxed conformation of a protein (e.g. PrP$^c$). This complexing agent may be a biological molecule such as a peptide or antibody, e.g. an antibody selective for PrP$^{Sc}$, or a chemical agent, e.g. phosphotungstic acid (PTA), which may be added in the form of a salt, e.g. sodium phosphotungstate. The complexing agents may be used singly or in combination. For example, a biological complexing agent may be used in tandem with a chemical complexing agent, such as the use of a peptide and a chemical agent. In another example, two complexing agents of the same class can be used together, e.g. a mixture of phosphotungstic acid (and salts thereof) and trichloroacetic acid. The complex formed must provide some means for separating the complex from the remainder of the composition, such as immobilization of the complexing agent to a surface. A preferred complexing agent which binds PrP$^{Sc}$ more readily than it binds PrP$^C$ and a particularly preferred agent binds PrP$^{Sc}$ with a high degree of affinity and does not bind PrP$^C$ at significant levels. Objectively, a preferred binding agent binds PrP$^{Sc}$ with twice or more the binding affinity as it binds PrP$^C$ and preferably five times or more the binding affinity as it binds PrP$^C$.

The terms "protein" as used herein is intended to encompass any amino acid sequence and include modified sequences such as glycoproteins. The term includes naturally occurring proteins and peptides as well as those which are recombinantly or synthetically synthesized. As used in connection with the present invention the term "protein" is specifically intended to cover naturally occurring proteins which occur in at least two different conformations wherein both conformations have the same or substantially the same amino acid sequence but have two or more different three dimensional structures. The two conformations of the protein include at least one conformation which is not related to a disease state and at least one conformation which is related to a disease state—pathogenic. A specific and preferred example of a protein as used in connection with this disclosure is a PrP protein which includes the non-disease form referred to as the PrP$^c$ form and the disease related form referred as the PrP$^{Sc}$. Although a prion protein or the PrP$^{Sc}$ form of a PrP protein is infectious and pathogenic, the disease conformation of other proteins is not infectious although it is pathogenic. As used herein, the term pathogenic may mean that the protein actually causes the disease or it may simply mean that the protein is associated with the disease and therefore is present when the disease is present. Thus, a pathogenic protein as used in connection with this disclosure is not necessarily a protein which is the specific causative agent of a disease.

The terms "PrP protein", "PrP" and like are used interchangeably herein and shall mean both the infectious particle form PrP$^{Sc}$ known to cause diseases (spongiform encephalopathies) in humans and animals and the noninfectious form PrP$^C$ which, under appropriate conditions is converted to the infectious PrP$^{Sc}$ form.

The terms "prion", "prion protein" and "PrP$^{Sc}$ protein" and the like we used interchangeably herein to refer to the infectious PrP$^{Sc}$ form of PrP, and is a contraction of the words "protein" and "infection." Particles are comprised largely, if not exclusively, of PrP$^{Sc}$ molecules encoded by a PrP gene. Prions are generally PrP$^{Sc}$ dimers. Prions are distinct from bacteria, viruses and viroids. Known prions infect animals to cause scrapie, a transmissible, degenerative disease of the nervous system of sheep and goats, as well as bovine spongiform encephalopathy (BSE), or "mad cow disease", and feline spongiform encephalopathy of cats. Four prion diseases known to affect humans are (1) kuru, (2) Creutzfeldt-Jakob Disease (CJD), (3) Gerstmann-Straussler-Scheinker Disease (GSS), and (4) fatal familial insomnia (FFI). As used herein "prion" includes all forms of prions causing all or any of these diseases or others in any animals used—and in particular in humans and domesticated farm animals.

The term "PrP gene" is used herein to describe genetic material which expresses proteins including known polymorphisms and pathogenic mutations. The term "PrP gene" refers generally to any gene of any species which encodes any form of a PrP protein. Some commonly known PrP sequences are described in Gabriel et al., Proc, Natl. Acad. Sci. USA 8:9097–9101 (1992), and U.S. Pat. Nos. 5,565,186; 5,763,740; 5,792,901; and WO97/04814, incorporated herein by reference to disclose and describe such sequences. The PrP gene can be from any animal, including the "host" and "test" animals described herein and any and all polymorphisms and mutations thereof, it being recognized that the terms include other such PrP genes that are yet to be discovered. The protein expressed by such a gene can assume either a PrP$^C$ (non-disease) or PrP$^{Sc}$ (disease) form.

The term "antibody" stands for an immunoglobulin protein which is capable of binding an antigen. Antibody as used herein is meant to include the entire antibody as well as any antibody fragments (e.g. F(ab)', Fab, Fv) capable of binding the epitope, antigen or antigenic fragment of interest. Preferred antibodies for assays of the invention are immunoreactive or immunospecific for and therefore specifically and selectively bind to a protein of interest e.g., a PrP protein and specifically a PrP$^{Sc}$ protein or PrP$^{Sc}$ dimer. Antibodies which are immunoreactive and immunospecific for both the native non-disease form and disease form (e.g., for both native PrP$^C$ and native PrP$^{Sc}$) may be used. Antibodies for PrP are preferably immunospecific—e.g., not substantially cross-reactive with related materials. Some specific antibodies which can be used in connection with the invention are disclosed in published PCT application WO 97/10505 which is incorporated herein by reference to disclose and describe antibodies. This published PCT application corresponds to U.S. Pat. No. 5,846,533 issued Dec. 8, 1998 also incorporated herein by reference. The term "antibody" encompasses all types of antibodies, e.g. polyclonal, monoclonal, and those produced by the phage display methodology. Particularly preferred antibodies of the invention are antibodies which have a relatively high degree of affinity for both native PrP$^C$ and PrP$^{Sc}$ and those with greater binding affinity for PrP$^{Sc}$ are preferred. An antibody of the invention is a "complexing agent" as defined herein.

An antibody for binding to PrP$^C$ is the monoclonal antibody 263K 3F4 produced by the hybridoma cell line ATCC HB9222 deposited on Oct. 8, 1986 in the American Type Culture Collection, 12301 Parklawn Drive, Rockville, Md. 20852 and disclosed and described in U.S. Pat. No. 4,806,627 issued Feb. 21, 1989—incorporated by reference to disclose antibodies which selectively bind PrP$^C$ but not PrP$^{Sc}$.

"Purified antibody" refers to that which is sufficiently free of other proteins, carbohydrates, and lipids with which it is naturally associated. Such an antibody "preferentially binds" to PrP$^{Sc}$ protein (or an antigenic fragment thereof), and does not substantially recognize or bind to other antigenically unrelated molecules. A purified antibody of the invention is preferably immunoreactive with and immunospecific for a specific species and more preferably immunospecific for native PrP$^{Sc}$.

"Antigenic fragment" of a protein (e.g., a PrP protein) is meant a portion of such a protein which is capable of binding an antibody.

By "binds specifically" is meant high avidity and/or high affinity binding of an antibody to a specific polypeptide e.g., epitope of a protein, e.g., a $PrP^{Sc}$. Antibody binding to its epitope on this specific polypeptide is preferably stronger than binding of the same antibody to any other epitope, particularly those which may be present in molecules in association with, or in the same sample, as the specific polypeptide of interest e.g., binds more strongly to epitope fragments of a protein such as $PrP^{Sc}$ so that by adjusting binding conditions the antibody binds almost exclusively to an epitope site or fragments of a desired protein such as an epitope fragment of $PrP^{Sc}$.

By "detectably labeled antibody", "detectably labeled anti-PrP" or "detectably labeled anti-PrP fragment" is meant an antibody (or antibody fragment which retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels known in the art, but normally are radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labeling antibodies, and methods for using labeled antibodies are well known in the art (see, for example, Harlow and Lane, eds. (Antibodies: A Laboratory Manual (1988) Cold Spring Harbor Laboratory Press, Cold Spring Harbor, N.Y.)). Europium is a particularly preferred label.

Abbreviations used herein include:
CNS for central nervous system;
BSE for bovine spongiform encephalopathy;
CJD for Creutzfeldt-Jacob Disease;
FFI for fatal familial insomnia;
GdnHCl for Guanidine hydrochloride;
GSS for Gerstamnn-Strassler-Scheinker Disease;
Hu for human;
HuPrP for human prion protein;
Mo for mouse;
MoPrP for mouse prion protein;
SHa for a Syrian hamster;
SHaPrP for a Syrian hamster prion protein;
$PrP^{Sc}$ for the scrapie isoform of the prion protein;
$PrP^{C}$ for the cellular contained common, normal isoform of the prion protein;
$PrP^{CJD}$ for the CJD isoform of a PrP protein;
FVB for a standard inbred strain of mice often used in the production of transgenic mice since eggs of FVB mice are relatively large and tolerate microinjection of exogenous DNA relatively well;
$[PrP_\beta]$—concentration of prion protein in β-sheet conformation;
[DRC]—concentration of a disease related conformation of a protein.
PTA—phosphotungstic acid
NaPTA—sodium phosphotungstate
TCA—trichloroacetic acid
AC—affinity chromatography

GENERAL ASPECTS OF THE INVENTION

Assays for the detection of prions are in development but not yet commercialized. Further, the cost, convenience or accuracy (on a large scale) of such assays has not yet been determined. Accordingly, when a material such as human plasma is suspected of containing prions it is destroyed—see The Wall Street Journal, Nov. 25, 1998 page 1 article entitled: "'Mad Cow' Fears Leads U.K. to Destroy Parts of all Donated Blood" indicating that England was destroying their supply of human plasma. This dramatic action was taken because (1) prions might be present in their human plasma, (2) prion diseases are fatal and not treatable at present, (3) no commercially available test for prions at present, and (4) no commercially available method of removing prions from a sample at present. The present invention includes a method of removing prions.

Some proteins such as the protein expressed by the PrP gene have more than one conformational shape. For example a PrP protein may assume its cellular form, i.e. $PrP^{C}$ form or its scrapies form, i.e. $PrP^{Sc}$ form. One form of the protein is harmless (e.g. $PrP^{C}$) whereas another form of the protein is pathogenic (e.g. $PrP^{Sc}$). When the constricted, pathogenic form of the protein such as $PrP^{Sc}$ is present in an animal in very small amounts the animal is not showing symptoms of disease. However, the animal will develop a disease related to the pathogenic form of the protein—e.g. develop a prion disease. To avoid progression and/or possible transmission of disease, it is important to remove any $PrP^{Sc}$ present in biological fluids, and particularly biological fluids that are to be introduced to a subject (e.g. blood products). The present invention is useful with respect to (1) eliminating the pathogenic form of the protein from the sample such that the material is rendered "prion free" and/or (2) reducing the concentration of the pathogenic form of the protein in a material to a level such that the material is rendered "non-infectious."

The present invention makes it possible to remove prions from a biological sample by exposing the sample to a complexing agent, which binds (preferably selectively) to $PrP^{Sc}$ and allows removal of the $PrP^{Sc}$. The present process is especially, though not exclusively, useful for the treating of and/or removal of $PrP^{Sc}$ from whole blood. Removal may be through complexing with an immobilized complexing agent, i.e. exposure of the sample to an affinity column, membrane, filter, or beads with immobilized complexing agent. The complexing agent will effectively remove the $PrP^{Sc}$ from the sample, while allowing the sample to stay substantially in the same form to allow proper use of the sample, i.e. maintaining proper pH, structural integrity of cells and proteins, and the like.

PROCEDURES IN GENERAL

Any type of sample can be processed using the present invention in order to remove a pathogenic form of a protein. Although the invention could be applied to removal of a constricted form of any protein having a constricted and relaxed form, the invention is described specifically with respect to removal of the pathogenic form of a PrP protein, i.e. concentrating and removing $PrP^{Sc}$.

A biological sample to be treated should be in a liquid flowable form at room temperature (15° C. to 30° C.). The solution should have a pH of about 6.4 to 8.4, preferably 7.4, and should not contain excess magnesium or calcium.

The next step is the most important in the process of the invention. A sample is exposed to a complexing agent which is immobilized on a solid surface or otherwise provided in a manner allowing separation of the prion-bound complexing agent from the sample. The complexing agent forms a complex with or somehow binds preferentially with or exclusively to any constricted (generally a pathogenic form) of the protein present in the sample, thus effectively immobilizing any $PrP^{Sc}$ present in the sample to the solid surface upon exposure of the sample to the immobilized complexing agent.

In one embodiment, a chemical agent such as a heteropoly acid (e.g. PTA), or preferably a metallic salt thereof (NaPTA) is immobilized to a solid surface such as a membrane filter, a magnetic bead, and the like. The sample is subjected to a the complexing agent over a period of time sufficient to allow substantially all the $PrP^{Sc}$ in the sample to complex with the PTA. For example, the sample could be incubated at about 30° C. to 45° C. (preferably 37° C.) over a period of from about 1 to 16 hours. The complexing agent forms a complex with the $PrP^{Sc}$. What is important is that complex formed can be separated away from the rest of the sample by some means, e.g. filtration, use of magnetic field, sedimentation and the like.

The process of the invention produces a biological sample wherein the $PrP^{Sc}$ or other pathogenic protein is substantially removed from the sample, and preferably to levels at which the $PrP^{Sc}$ is undetectable by conventional means. Methods of removal of the $PrP^{Sc}$ will prevent trransmission of $PrP^{Sc}$-mediated disorders by providing biological samples which are free from infectious levels of prions, i.e. "prion free."

COMPLEXING AGENTS

Compounds which are useful as complexing agents in the present invention include antibodies, enzymes, peptides, chemical species, binding molecules, etc. These complexing agents are used in a manner that allows binding and removal of prions from a biologial solution, while maintaining the essential elements of the biological material intact, e.g. retention of cellular morphology and protein integrity. Such complexing agents may be used in whole blood, in blood components such as plasma and platelets, and in other biological fluids as will be apparent to one skilled in the art.
Chemical agents In one embodiment of the invention, the compound for removal of prions from a biological material is a chemical agent that precipitates $PrP^{Sc}$. One preferred class of chemical agents for use as complexing agents in the present invention are heteropoly acids and salts thereof Heteropoly acids are fully or partially protonated forms of oxyanions having at least one central element and at least one coordinating element. Heteropoly acids may have the Keggin or Dawson structures.

A particular class of heteropoly acids is the protonated form of heteropolymolybdates. These anions contain from 2 to 18 hexavalent molybdenum atoms around one or more central atoms. About 36 different elements have been identified as central atoms of these heteropolymolybdates. These anions are all highly oxygenated. Examples of heteropolymolybdates include $[PMo_{12} O_{40}]^3$, $[As_2Mo_{18} O_{62}]^6$, and $[TeMo_6 O_{24}]^6$, where the central atoms are $P^{5+}$, $As^{5+}$, and $Te^{6+}$, respectively. A more detailed discussion of heteropolymolybdates is provided in the Kirk-Othmer Encyclopedia of Chemical Technology, 3rd ed., 15, 688–689 (1981).

Another class of heteropoly acids, which is analogous to the protonated form of heteropolymolybdates, is the protonated form of heteropolytungstates. In heteropolytungstates, the coordinating element is tungsten instead of molybdenum. U.S. Pat. No. 4,376,219, the entire disclosure of which is expressly incorporated herein by reference, discusses the preparation of various heteropoly acids. The central elements of these heteropoly acids may be selected from the group consisting of P, Si, B, Ge, As, Se, Ti, Zr, Mn, F, V, Ce, and Th. The coordinating elements of these heteropoly acids include Mo and/or W. Optional coordinating elements include V, Mn, Co, Ni, Cu, Zn, and Fe. The ratio of the number of the coordinating elements to the number of central elements may be from 2.5 to 12, preferably from 9 to 12. Particular heteropoly acids, which are exemplified in U.S. Pat. No. 4,376,219, include phosphotungstic acid, silicotungstic acid, 10-tungsto-2-vanadophosphoric acid, 6-tungsto-6-molybdophosphoric acid, phosphomolybdic acid, silicomolybdic acid, germanotungstic acid, tungstofluoric acid, and 18-tungsto-2-phosphoric acid as well as salts of all or any of these acids e.g. metal salts such as Na, K, Mg, and Ca salts. A particular heteropoly acid for use in the present invention is phosphotungstic acid, i.e., $H_3PW_{12}O_{40}$ and its metal salts particularly Na salts. Such complexing agents effectively bind to $PrP^{Sc}$.

Such chemical agents may be used alone, in combination, or with other non-bioactive chemicals such as buffers and inert binding chemicals. Heteropoly acids of the invention (e.g. PTA) are preferably, although not exclusively, used in a metallic salt form. The metallic salt includes, but is not limited to, sodium, potassium, calcium and the like.

The amount of heteropoly acid or salt thereof which is combined with the present support material should be present in an amount sufficient to significantly remove $PrP^{Sc}$ from the a biological fluid, and preferably in an amount sufficient to remove $PrP^{Sc}$ to undetectable levels or at least non-infectious levels. The weight ratio of heteropoly acid to support material may be, for example, from about 1:20 to about 1:1. The heteropoly acid may be combined with the support material in any manner which provides adequate dispersion of the heteropoly acid, thereby increasing the effective surface area of the heteropoly acid. A preferred technique for combining these components is by impregnation of the support material with the heteropoly acid. The heteropoly acid may also be combined with the support material by an ion exchange technique. The impregnation technique may involve sorbing an aqueous solution of the heteropoly acid into the porous region of the support material followed by drying to remove water and to leave behind supported heteropoly acid. Other methods of immobilizing heteropoly acids or salts thereof may be used to immobilize these complexing agents, as will be apparent to one skilled in the art upon reading this disclosure.
Biological agents In another embodiment, the complexing agent is a protein, peptide, or other biological moeity that selectively binds to $PrP^{Sc}$.

In one embodiment, the complexing agents are peptides or other small molecules designed to selectively bind to prions. Preferably, the peptides or small molecules are designed to preferentially bind to $PrP^{Sc}$. By "preferentially bind" is meant that the peptide is designed to be at least 20 times or more, more preferably 50 times or more, more preferably 100 times or more, and even more preferably 1000 times or more likely to bind to $PrP^{Sc}$ than to other proteins in the biological solution. Peptides of the invention are preferably designed to bind to the native form of $PrP^{Sc}$, as opposed to the denatured form, since the biological fluids generally contain $PrP^{Sc}$ in native form. Peptides may be designed to maximize binding to $PrP^{Sc}$ by designing the peptides to areas of $PrP^{Sc}$ that are more accessible to binding, as can be predicted by one skilled in the art. Useful antibodies which bind $PrP^{Sc}$ are disclosed and described in U.S. Pat. No. 5,846,533 issued Dec. 8, 1998 incorporated herein to disclose and describe antibodies and methods of making antibodies. Portions of these antibodies which bind to $PrP^{Sc}$ are peptides which can be bound to a support surface and used in the present invention.

Alternatively, peptides may be designed to bind selectively to $PrP^C$ or to both $PrP^{Sc}$ and $PrP^C$. Although the $PrP^{Sc}$ form of the prion is the infectious portion, removal of the normal cellular prion proteins can also effectively halt or slow the progression of a prion-mediated disorder.

The complexing agent of the invention may also be an antibody selective for prions. This antibody may be directly immobilized or may be bound to another component (e.g. a high density metal). That antibody may bind to $PrP^{Sc}$, e.g. the antibody disclosed in U.S. Pat. No. 5,846,533. To remove $PrP^C$ present in the sample, an antibody which binds selectively or exclusively to $PrP^C$ may be used. Such an antibody is disclosed in U.S. Pat. No. 4,806,627, issued Feb. 21, 1989, disclosing monoclonal antibody 263K 3F4, produced by cell line ATCC HB9222 deposited on Oct. 8, 1986, which is incorporated herein by reference. The cell line producing the antibody can be obtained from the American Type Culture Collection, 12301 Parklawn Drive, Rockville, Md. 20852.

In general, scrapie infection fails to produce an immune response, with host organisms being tolerant to $PrP^{Sc}$ from the same species. Antibodies which bind to either $PrP^C$ or $PrP^{Sc}$ are disclosed in U.S. Pat. No. 5,846,533. Any antibody binding to $PrP^C$ and not to $PrP^{Sc}$ can be used, and those skilled in the art can generate such using known procedures, e.g., see methods of producing phage display antibody libraries in U.S. Pat. No. 5,223,409. Polyclonal anti-PrP antibodies have though been raised in rabbits following immunization with large amounts of formic acid or SDS-denatured SHaPrP 27-30 [Bendheim, Barry et al. (1984) *Nature* 310:418–421; Bode, Pocchiari et al. (1985) *J Gen Virol* 66:2471–2478; Safar, Ceroni et al. (1990) *Neurology* 4:513–517]. Similarly, a handful of anti-PrP monoclonal antibodies against PrP 27-30 have been produced in mice [Barry and Prusiner (1986) *J Infect Dis* 154:518–521; Kascsak, Rubenstein et al. (1987) *J Virol* 61:3688–3693]. These antibodies were generated against formic acid- or SDS-denatured PrP 27-30 and are able to recognize native $PrP^C$ and treated or denatured $PrP^{Sc}$ from both SHa and humans equally well, but do not bind to MoPrP. Not surprisingly, the epitopes of these antibodies were mapped to regions of the sequence containing amino acid differences between SHa- and MoPrP [Rogers, Yehiely et al. (1993) *Proc Natl Acad Sci USA* 90:3182–3186].

It is not entirely clear why many antibodies of the type described in the above cited publications will bind to $PrP^C$ and treated or denatured $PrP^{Sc}$ but not to native $PrP^{Sc}$. Without being bound to any particular theory it is believed that such may take place because epitopes which are exposed when the protein is in the $PrP^C$ conformation are unexposed or partially hidden in the $PrP^{Sc}$ configuration—where the protein is relatively insoluble and more compactly folded together.

For purposes of the invention an indication that no binding occurs means that the equilibrium or affinity constant $K_a$ is $10^6$ l/mole or less. Further, binding will be recognized as existing when the $K_a$ is at $10^7$ l/mole or greater, preferably $10^8$ l/mole or greater. The binding affinity of $10^7$ l/mole or more may be due to (1) a single monoclonal antibody (i.e., large numbers of one kind of antibodies) or (2) a plurality of different monoclonal antibodies (e.g., large numbers of each of five different monoclonal antibodies) or (3) large numbers of polyclonal antibodies. It is also possible to use combinations of (1)–(3). Selected preferred antibodies will bind at least 4-fold more avidly to the treated or denatured $PrP^{Sc}$ forms of the protein when compared with their binding to the native conformation of $PrP^{Sc}$. The four fold differential in binding affinity may be accomplished by using several different antibodies as per (1)–(3) above and as such some of the antibodies in a mixture could have less than a four fold difference.

A variety of different methods may be used with one or more different antibodies. Those with skill in the art will recognize that antibodies may be labeled with known labels and used with currently available robotics, sandwich assays, electronic detectors, flow cytometry, and the like. Further, the antibodies may be bound to denser components directly or via other intermediates such as anti-antibodies.

METHODS OF PURIFICATION

The complexing agent of the invention may be used in a variety of purification procedures to effectively remove prions from a biological material. A number of methods for use in the present invention are summarized as follows.

Affinity Chromatography

Affinity chromatography (AC) relies on the interaction of the protein with an immobilized ligand. AC is predicated, in part, on the interaction of ligands attached to chromatographic supports. A hydrophobic ligand coupled to a matrix is variously referred to herein as an AC support, AC gel or AC column. It is further appreciated that the strength of the interaction between the protein and the AC support is not only a function of the proportion of non-polar to polar surfaces on the protein but by the distribution of the non-polar surfaces as well.

A number of matrices may be employed in the preparation of AC columns. Preferably, such matrices are beads, and more preferably spherical beads, which serve as a support surface for the complexing agent of the invention. Suggested materials for the matrices include agarose, cross linked dextran, polyhydroxyl ethyl methacrylate, polyacrylamide, cellulose, and derivatives or combinations thereof, preferably in the form of porous spheres. Cellulose acetate has previously been successfully used in devices for purification of biolological fluids, e.g. extracorporeal blood purification devices. Polyurethane is particularly blood compatible. Silica and its derivatives are also especially useful as support material for use with heteropoly acids. See U.S. Pat Nos. 5,475,178 and 5,366,945, which are incorporated herein by reference.

The preferred material for use in the methods of the present invention is agarose, a naturally occurring hydrophilic polymer. A beaded gel with a porosity of from 90–96% is formed by varying the percentage of agarose. The molecular weight of the gel ranges from 0.5 million for 10% agarose to 20 million for 4% agarose. Particle diameters ranging from 20 to 200 microns are commercially available. The mechanical strength of agarose beads can be increased by either increasing the percentage of agarose or crosslinking the beads with epichlorohydrin or 2,3 dibromopropanol, using the method of J. Porath et al. in J. Chromat 60, 167 (1971). This allows a corresponding increase in the maximum operating pressure (a fifty percent increase in agarose leads to a two to four fold increase in the maximum operating pressure).

The criteria to determine the appropriate coupling method are: minimization of leakage of the complexing agent from the support, maintenance of the thermal stability of the compound, and retention of the optimum amount of complexing agent. The technique must also not cause a deterioration in the support material or the production of reactive groups on the support which would bind blood components in vivo. The complexing agent must also retain its activity over time.

Further factors which must be considered in optimizing the affinity chromatography coupling method are: the extent of distribution of the coupling agent within the particles and/or columns; pH; temperature; the flow speed of the biological sample through the column; the size of the bound complexing agent; and/or the diameter and pore size of the particular support. Each of these conditions can be optimized for a particular procedure, biological sample, and complexing agent as will be apparent to one skilled in the art.

The AC composition of the present invention can be contained within a filtration cartridge for easy use of the composition in a biological fluid purification process. When the column composition is contained within a single cartridge, it can easily and conveniently be replaced when the purifying capacity of the composition becomes exhausted. Alternatively, the cartridge may be an integral part of a purifying device, in which case the entire device is replaced once the filtration composition has exhausted its efficacy. The support particles with the complexing agent are placed within the cartridge, and the solution to be reacted with the complexing agent is then circulated through the cartridge. Commercially available units for dialysis, blood exchange or oxygenation can be adapted for use as the purifying device.

Filtration Methods

Another method that may be used to remove prions from a biological sample involves filtration through a membrane. The membrane may have the prion complexing agent conjugated directly to the membrane, either on the side facing the biological fluid or more preferably on the side away from the biological fluid. Alternatively, the complexing agent may be compartmentalized in an area behind the membrane which is inaccessible to the larger components of the biological materials, e.g. blood cells. In the latter example, the complexing agent can be bound to an insoluble matrix behind the membrane. The membrane for use in the present invention may be in planar form, in the form of one or more hollow fibers, and/or in the form of flat foils. See U.S. Pat No. 4,361,484, which is incorporated herein by reference.

Suitable materials for the membrane include regenerated cellulose, cellulose acetate, non-woven acrylic copolymer, polysulphone, polyether sulphone, polyacrylonitrile, polyamide and the like. The biologically active material is immobilized in the pores and/or on the surface of the side of the membrane that faces away from the biological fluid. Thereby the components such as blood corpuscles are prevented from contacting the active material. The pores of the membrane are usually of the magnitude of order of 0.01 to 0.8 microns, preferably 0.15 to 0.45 microns. the polymer support must be stable under the conditions of its planned use, i.e. it should not be chemically or enzymatically degraded by blood, the support and immobilized complexing agent must be blood compatible, and the support should have good flow characteristics and low compressibility under clinical flow rates in the range of 150–250 ml/min.

Through the above construction of the microporous membrane, i.e. asymmetric immobilizing of the prion complexing agent, the biological fluid need not be exposed to any following filtering for removing possible remaining harmful residues. As well the separation as the removal of the substances can thereby be performed in one and the same step.

The microporous semipermeable membrane can be in the form of individual fibers which are bundled and encapsulated within one and the same casing, with an inlet and outlet for the biological fluid. The ends of the fibers are glued by means of a suitable binder to retain the individual fibers essentially parallel within the casing. One end of the fibers or bundles of fibers is provided in communication with the inlet, while the opposite end is provided in communication with the outlet.

The biological material is pumped into the casing through the inlet and through the longitudinal void of the fibers and out of the casing through the outlet. During the passage through the casing the fluid is exposed to the pressure variations, such that only a penetrating fraction is caused to flow in an alternating path through the fiber walls in each direction for contacting with the prion complexing material. The means for the realization of the pressure variations may again be made up of an expansion chamber in communication with the space between the individual fibers and bundles of fibers, respectively. Any subsequent filtering of the biological material for the removal of possible harmful residues is not needed, since the filtering is automatically achieved through the passage of the fluid through the fiber walls.

The pressure variations may vary from −200 to +200 mmHg, preferably from −100 to +100 mmHg. The longer the diffusion distance for the blood, for example if the prion complexing agent is bound to an unsoluble matrix behind the membrane, the higher compensating pressure variations are required to achieve the desired separation effect. In a corresponding way the frequency of the pressure variations may vary from about 0.05 up to about 10 Hz, preferably 0.5 to 1 Hz. After the passage through the treating unit the biological material, e.g. whole blood, may reinserted in the patient directly, or may be stored for future use. Treated blood may be stored whole, or may be stored in its various components, e.g. plasma, platelets, erythrocytes, etc. Alternatively, the blood may be separated into its components prior to removal of prions.

When the complexing agent is an antibody, it is often desirable to have a molecular spacer segment forming means for spacing the antibody from the wall of the exterior porous side of the hollow fiber membrane. This general arrangement is preferred when the molecular weight of the antigen is large, e.g., 100,000 Daltons or higher in molecular weight. For example, a six- or eight-carbon methylene group is convenient as a spacer or "handle" between antibody and membrane surface. When an antigen is readily absorbed by albumin or more readily chemically reacted with albumin than with the material of the filter membrane surface, the spacer molecule may be a protein such a albumin. The outer surface of a membrane can be considered a relatively porous material compared to that of the interior surface which is normally the effective filter surface of an ultrafilter membrane of the asymmetric, sometimes called anisotropic, type. Thus, for example, the exterior, porous side of a membrane may be treated with a 17% human albumin solution in saline. The albumin will coat the surfaces within the porous zone of the membrane structure (i.e. the zone that underlies the barrier layer of the membrane) and, thereafter, a solution of protein (e.g. a $PrP^{Sc}$ antibody) can be deposited upon the albumin. Often it is desirable to crosslink the protein somewhat (as with a dilute glutaraldehyde solution or some other such mild crosslink-inducing agent); this aids in anchoring the material in place on the membrane surface.

One approach to preparing a cartridge which is capable of removing pathogenic factors from blood is an extracorporeal circulation system with fiber membranes having sufficient permeability for the pathogenic blood factor to be removed through the membrane and into a soluble, immobilized antibody sequestered in the extrafiber space. This involves the formation of a high molecular weight polymeric conjugate of the $PrP^{Sc}$ antibody and $PrP^{Sc}$ that cannot cross the filtration side of the membrane into the remainder of the biological sample, i.e. where the cells are maintained.

In order to form a soluble, immobilized complexing agent the molecular weight of the immunoreactive complexing agent may be increased to such a size that it will not diffuse, from the exterior, porous, portion of the fiber and into the blood to be purified. This can be done by chemically reacting the complexing agent with a high molecular weight, water-soluble substance such as silica gel or dextran or by polymerizing the immunoreactive complexing agent. The use of such macromolecular-borne antibodies is advantageous for high rate of antigen absorption, due to enhanced rate of polarization effects on mass transfer and binding kinetics.

Alternatively, the membrane may be composed of two membrane halves which are mechanically generally identical to each other but which chemically may be built up of different material. In this case, it is enough if only the membrane half that faces away from the biological material is able to bind to the prion complexing agent. For example, the membrane halves may be provided in an abutting relationship to each other, wherein the $PrP^{Sc}$ complexing agent preferably is bound in the pores and on both surfaces of the membrane half that faces away from the biological material.

The complexing agent (e.g. NaPTA or anti-$PrP^{Sc}$ antibodies) can also be immobilized in the membrane so that the surface that faces towards the biological material is free of the contacting reagent. This is to avoid contact between blood corpuscles and the reagent and thereby pyrogen and/or anaphylactic reactions. Thus it is a form of a symmetric immobilization, where on one surface of the membrane (as well as in the pores) the prion complexing agent is immobilized. The advantage of immobilizing within the pores of the membrane is that the active microscopic surface may be manifolded (>1000) compared to the macroscopic surface. Since the complexing agent is immobilized in the part of membrane that faces away from the biological material the biological material will not come into contact with the material. Consequently, any following separate filtering of the biological material therefore is not necessary.

Alternatively, the prion complexing agent may be bound to an unsoluble matrix behind the membrane. The treating process is yet similar, but since the necessary diffusion distance is about 10 times longer, it may be necessary to arrange a somewhat more real flow through the membrane.

Irrespective of whether the prion complexing agent is immobilized in the pores or immobilized to an insoluble matrix behind the membrane, the immobilizing procedure is preferably performed such that the complex of prions and the complexing agent remains bound and immobilized, i.e. it is not present in the blood following the purification technique. Generally, covalent coupling is the safest immobilization. The nature of covalent coupling used depends on the choice of membrane material and the nature of the complexing agent.

Magnetic Particles

Prions can also be removed from biological materials using magnetic partcles comprised of prion complexing agent. The principle components of the magnetic particles of the present invention are a magnetic core. The core consists of particles of iron oxide or other magnetic materials. The $PrP^{Sc}$ binding agent of the invention can be incorporated directly on the magnetic core, or indirectly incorporated onto the magnetic core, e.g. through the use of a fibrous material and a binding agent. The fibrous material may comprise an organic polymer in the form of fibers, such as carbohydrate polymers, urea formaldehyde or polynonamethylene urea, and, in particular, cellulose fibers. The binding agent is a material which is introduced between the magentic core and the fiber strands as a liquid, or in solution, and is solidified during the production process of freezing, polymerization or evaporation of a solvent. Examples of suitable binding agents are agar, gelatin, an epoxy resin or urea formaldehyde furfuryl alcohol.

Magnetic microparticles useful in the present method can be a variety of shapes, which can be regular or irregular; preferably the shape maximizes the surface areas of the microparticles. The magnetic microparticles should be of such a size that their separation from solution, for example by filtration or magnetic separation, is not difficult. In addition, the magnetic microparticles should not be so large that surface area is minimized or that they are not suitable for microscale operations. Suitable sizes range from about 0.1.mu. mean diameter to about 100.mu. mean diameter. A preferred size is about 1.0.mu. mean diameter. Suitable magnetic microparticles are commercially available from PerSeptive Diagnostics and are referred to as BioMag COOH (Catalog Number 8-4125).

The coated magnetic particles of the present invention can be produced by stirring or mixing the core particles in a suspension comprising a fibrous material, a prion complexing agent, and a binding agent. The fibers attach to the core particles and the binding agent fills the interstices. The binding agent is then solidified by one of the means as discussed above, in such a manner that the prion complexing agent is accessible on the outer surface. An example of such a system which uses iron oxide as the core particles, cellulose fibers as the fibrous material and agar as the binding agent is described in U.S. Pat. No. 5,705,628, which is incorporated herein by reference.

The present invention also includes within its scope a composite magnetic resin which comprises magnetic particles embedded in a organic polymer matrix which either contains, or has attached thereto, sites which are selective for prions.

The composite may thus comprise magnetic particles embedded in a polymeric resin which contains active sites or chemicals intended to selectively absorb to prions. For example, the polymeric resin has small particles of selective absorbers bound thereto. The selective absorbers may be, for example, a metal salt of phosphotungtic acid.

The composite magnetic particles of the present invention may be used in a method for the removal of prions from any flowable biological sample. Removal of prions from the human product is by contacting the solution to be treated with particles of a composite magnetic resin with immobilized complexing agent and separating by magnetic filtration the composite magnetic resin particles from the solution. These magnetic particles may be used once and discarded, or recycled for use in purifying other blood products. Particles can be recycled by subjecting the separated composite magnetic resin particles to regeneration using an appropriate regenerant solution, separating the regenerated composite magnetic resin particles from the regenerant solution.

The composite magnetic resin particles with bound prions are then selectively removed from the solution by magnetic filtration using techniques which are known in the art. The composite magnetic resin particles are then recovered from the filter and the prions removed therefrom using an appropriate regenerant solution, for example an acidic solution. The cleaned composite magnetic resin particles can then be recovered from the regenerant solution by magnetic filtration and the clean particles recycled for additional use.

Purification of biological material from a patient may be through an extracorporal treatment unit, and following treatment the purified fluid may either be stored or may be reintroduced to the patient. The biological material is pumped from for example a patient into a treating unit comprising a microporous semipermeable membrane having pores of 0.01–0.8 microns, preferably 0.15–0.45 microns. During the passage through the treating unit the biological material is exposed to pressure variations (for example from −200 to +200 mmHg, preferably from −100 to +100 mmHg), whereby a penetrating fraction of the biological material, e.g. the plasma, is caused to flow in an alternating path through the membrane wall in each direction for contacting the complexing agent.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Spherical beads composed of a silicate derivative are used in a cylindrical metal chromatography apparatus. The beads are prepared for affinity chromatography by impregnation of the beads with PTA prior to placement within the chromatography housing apparatus. Beads of approximately 5 mm were impregnated with 25 wt. % loading of $H_3PW_{12}O_{40}$ by the incipient wetness method. The coated beads are dried in a vacuum oven to remove the excess water. Finally, these coated beads are calcined at 350° C. for 1 hour in nitrogen and 4 hours in air.

The coated spherical beads are cooled to approximately 37° C., placed in the chromatography column apparatus, and equilibrated with 20 mM sodium phosphate at pH 7. A preparation of human plasma is added to the mixture, which is allowed to run over the column at a speed sufficient for binding of prions to the immobilized PTA. An aliquot of the purified plasma is then tested for the presence of prions using Western blot analysis.

Example 2

An amine substituted nylon membrane is manufactured as follows as described in U.S. Pat No. 4,361,484, which is incorporated herein by reference. Antibody selective for prion is coupled to the amine substituted membrane for use in filtration. The IgG portion of the $\alpha$-$PrP^{Sc}$ molecule is immobilized on the membrane using glutaraldehyde. The membrane is treated with 2.5% solution of glutardialdehyde in 0.1 M phosphate buffer at pH=6.8, rinsed with distilled water and dried. A solution containing $\alpha$-$PrP^{Sc}$ is dissolved in 0.1 mM phosphate buffer (pH=6.0, 4° C.) and the solution is incubated with the treated membrane. Coupling of the antibody with the membrane is allowed to take place for 15 hours at 4° degrees C. Following incubation, the membrane is rinsed in distilled water, and the unbound $\alpha$-$PrP^{Sc}$ is collected with the first rinsing water for later use.

The membrane with bound $\alpha$-$PrP^{Sc}$ is then used in a hemofiltration apparatus to remove the $PrP^{Sc}$ protein from human blood. The $\alpha$-$PrP^{Sc}$-bound filter is placed into a hemofiltration device, such as that described in U.S. Pat Nos. 5,858,238, 5,855,782, and 5,851,394 each of which are incorporated herein by reference.

Example 3

One method for purifying blood of a living animal involves passing the blood through an extracorporeal shunt device. A shunt device is constructed for this purpose with cellulosic hollow fibers having an ID of 200 u and inner wall thickness of 30 micrometers. The cartridge formed has a total tube inner surface area of 0.6 square meter.

The hollow fibers are perfused with a solution of an anti-$PrP^{Sc}$ antibody in saline buffered with borate to maintain pH 8.5. After three hours of recirculation, the cartridge is washed extensively with saline. The solution is assayed for Anti-$PrP^{Sc}$ antibody by immunodiffusion technique, known to the art, before and after the recirculation step in order to evaluate the degree of antibody uptake by the fiber wall. Subsequently the cartridge is dried in a nitrogen stream, placed in a plastic bag and sealed.

A cartridge containing 1,000 asymmetric hollow fibers having a cut-off pore-size at 500,000 Dalton MW and inner diameter of 150–200 microns is washed by pumping saline solution through the fiber walls from the outside in the "reverse" ultrafiltration mode. Thereafter a 1% solution of human serum albumin is pumped through the fiber wall in the same way in order to deposit a monomolecular layer of albumin at the porous surface of the external side of the tubular membrane. Thereafter the solution of anti-$PrP^{Sc}$ antibody is filtered through the walls of hollow fibers in "reverse" direction to allow the antibodies to bind directly at the external side of the membrane or in close proximity of the membrane in the external region. The activity of the solution before filtration and that of the filtrate leaving the lumen is assayed for anti-$PrP^{Sc}$ antibody. The balance gives the amount of immunological activity deposited in the cartridge. After flushing the lumen space of the hollow fiber with streptomycin and saline, the cartridge is placed into a plastic bag and sealed. Cartridges so prepared are used in extracorporeal shunts.

Example 4

Super-paramagnetic polystyrene beads containing magnetite (average diameter 0.8.mu.m, 67% magnetic content—Sigma Chemical Co.) are coated overnight at room temperature with a monoclonal antibody raised native $PrP^{Sc}$. The resultant antibody-coated beads are placed into an apparatus comprised of a container such as a syringe body containing a support matrix surrounded by a helically wound copper wire coil, which is connected a suitable supply of alternating electric current via suitable switch means.

A 10 ml sample of bovine blood containing prion protein was added to the beads and incubated for 10 minutes (in the presence of the applied magnetic field). An A/C field (50 Hz, 50 volts) was applied to the coil to generate a magnetic field, and the magnetic beads were isolated from the blood. Complexed beads tested for the presence of prions by immuno-fluorescence staining techniques using an anti-PrP fluorescent FITC conjugate (Bradsure Biochemicals Ltd.). Prion complexes detectable using the procedure clearly indicate that specific capture of the prions is achieved.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of separating prions from a sample, comprising the steps of:

contacting a sample in a flowable liquid state with a solid substrate comprised of a prion complexing agent comprised of a heteropoly acid or a salt thereof;

allowing the sample to remain in contact with the substrate for time such that prions in the sample bind to the substrate; and separating the sample from the substrate.

2. The method of claim 1, wherein the heteropoly acid or salt thereof is a metal salt of phosphotungstic acid.

3. The method of claim 1, wherein the sample comprises a human body fluid.

4. The method of claim 1, wherein the sample comprises human blood.

5. The method of claim 1, wherein the substrate is further comprised of a metal.

6. The method of claim 5, wherein the substrate is further comprised of a polymer coated on the metal.

7. The method of claim 5, wherein the substrate is in the shape of spherical beads.

8. The method of claim 6, wherein the metal is a ferromagnetic metal.

9. The method of claim 8, wherein the separating is carried out by application of magnetic energy.

* * * * *